United States Patent
Tang et al.

(10) Patent No.: US 10,092,318 B2
(45) Date of Patent: Oct. 9, 2018

(54) TRANS-ENDOSCOPIC AND LAPAROSCOPIC SURGERY PORT

(71) Applicant: Tanam Medical Inc., Victoria (CA)

(72) Inventors: Bao Tang, Victoria (CA); Brad J. Amson, Victoria (CA)

(73) Assignee: Tanam Medical Inc., Victoria, British Columbia ( * ) Notice: Subject to any disclaimer, the term of this patent is extended or adjusted under 35 U.S.C. 154(b) by 0 days.

(21) Appl. No.: 15/285,010

(22) Filed: Oct. 4, 2016

(65) Prior Publication Data

US 2017/0086880 A1    Mar. 30, 2017

Related U.S. Application Data

(62) Division of application No. 14/404,508, filed as application No. PCT/CA2013/000156 on Feb. 20, 2013, now Pat. No. 9,486,198.

(Continued)

(30) Foreign Application Priority Data

Jun. 6, 2012    (CA) ..................................... 2778976

(51) Int. Cl.
*A61B 17/34* (2006.01)
*A61B 17/02* (2006.01)
(Continued)

(52) U.S. Cl.
CPC ...... *A61B 17/3423* (2013.01); *A61B 17/0218* (2013.01); *A61B 90/40* (2016.02); *A61M 39/0247* (2013.01); *A61B 2017/349* (2013.01); *A61B 2017/3445* (2013.01); *A61B 2017/3466* (2013.01); *A61M 2039/027* (2013.01);
(Continued)

(58) Field of Classification Search
CPC ............ A61B 17/0218; A61B 17/3423; A61B 2017/0212; A61B 2017/0225; A61B 2017/3429; A61B 2017/3449
See application file for complete search history.

(56) References Cited

U.S. PATENT DOCUMENTS 5,545,179 A * 8/1996 Williamson, IV ......................... A61B 17/3423
600/32
7,008,377 B2    3/2006 Beane
(Continued)

FOREIGN PATENT DOCUMENTS

CA    2485106 A1    11/2003
CA    2648409 A1    1/2009
(Continued)

OTHER PUBLICATIONS

European Search Report dated Apr. 11, 2016 issued in corresponding European application No. 13752423.7.
(Continued)

*Primary Examiner* — Olivia C Chang
(74) *Attorney, Agent, or Firm* — McCarthy Tétrault LLP

(57) ABSTRACT

Surgical access ports useful in minimally invasive surgical procedures are provided. The access ports comprise a cannula that defines a passageway for one or more surgical instruments through a tissue tract and a dome extending from the cannula to provide an expanded diameter for receiving one or more surgical instruments.

19 Claims, 10 Drawing Sheets

Related U.S. Application Data

(60) Provisional application No. 61/601,863, filed on Feb. 22, 2012.

(51) Int. Cl.
  *A61B 90/40* (2016.01)
  *A61M 39/02* (2006.01)

(52) U.S. Cl.
  CPC ............... *A61M 2039/0261* (2013.01); *A61M 2039/0279* (2013.01); *A61M 2039/0297* (2013.01)

(56) References Cited

U.S. PATENT DOCUMENTS

| | | |
|---|---|---|
| 2005/0049624 A1 | 3/2005 | Francese et al. |
| 2006/0211992 A1 | 9/2006 | Prosek |
| 2007/0085232 A1 | 4/2007 | Brustad |
| 2009/0093850 A1 | 4/2009 | Richard |
| 2009/0192465 A1 | 7/2009 | Smith |
| 2010/0094227 A1 | 4/2010 | Albrecht et al. |
| 2010/0113886 A1 | 5/2010 | Piskun et al. |
| 2010/0312061 A1 | 12/2010 | Hess et al. |
| 2012/0022333 A1 | 1/2012 | Main et al. |
| 2013/0190574 A1 | 7/2013 | Smith |

FOREIGN PATENT DOCUMENTS

| | | |
|---|---|---|
| WO | 2011072098 A2 | 6/2011 |
| WO | 2011079374 A1 | 7/2011 |

OTHER PUBLICATIONS

International Search Report and Written Opinion received in PCT Application No. PCT/CA2013/000156, dated May 9, 2013.

\* cited by examiner

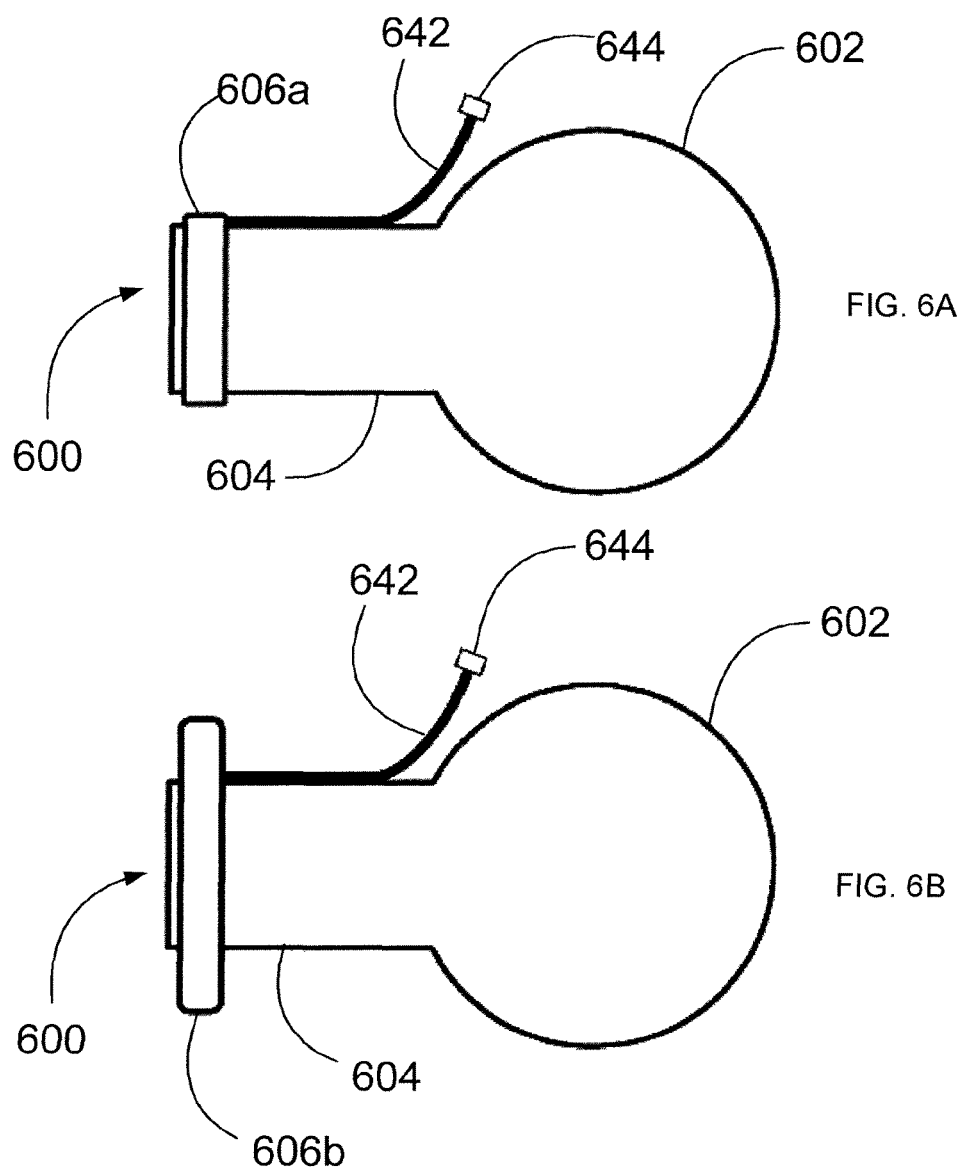

TRANS-ENDOSCOPIC AND LAPAROSCOPIC SURGERY PORT

CROSS REFERENCE TO RELATED APPLICATION

This application is a divisional application of U.S. patent application Ser. No. 14/404,508 filed on Nov. 28, 2014, the entirety of which is hereby incorporated by reference.

FIELD OF THE INVENTION

The present invention pertains to the field of surgical devices and more specifically, to an access port useful in minimally invasive surgical procedures such as laparoscopic and/or (trans-) endoscopic procedures.

BACKGROUND OF THE INVENTION

Minimally invasive surgery, such as endoscopic and/or laparoscopic procedures, is a type of surgery performed through one or more small incisions in a patient's body, usually less than an inch in dimension. Some advantages of minimally invasive surgery are that patients experience reduced physical and physiological trauma, much smaller scarring, and faster post-surgery recovery times.

The single port approach to minimally invasive surgery, whether that be through a single incision or via a natural orifice such as the oral cavity, nasal passages, the navel, the vagina, and the anus, for example, provides the benefit of smaller and fewer body cavity incisions. Single-port procedures, however, require several instruments to be inserted and manipulated through a single entry into a tissue tract, thereby, limiting the freedom of movement for manipulating the multiple instruments inserted through a single port.

Access ports are commonly used in such minimally invasive surgical procedures to facilitate the introduction and manipulation of multiple instruments and equipment into a tissue tract through an incision or a natural orifice. The access ports are used to protect adjacent tissues from potential abrasion and/or tearing and/or incised damage caused by insertion and manipulation of the surgical instruments and equipment. Some procedures involve the use of insufflation gases to enlarge the area surrounding the target surgical site to create a larger, more accessible work area. Accordingly, access ports may be introduced into regions that require maintenance of the pressurized gas.

Current surgical access ports allow for single instrument access through each port, or allow for multiple instrument access through a rigid or semi-rigid cannula. These devices do not provide flexibility to the surgeon in selecting instrument size, and they restrict instrument movement with their rigid cannulas.

Access ports that allow for a wider range of motion of the multiple instruments inserted in a single entry port have been described. For example, United States Patent Publication No. 2010/0113886 describes a surgical port comprising tubular cannulas through which surgical instruments are inserted. The tubular cannulas are flexible in a region of attachment to the carrier enabling pivoting and swiveling of the surgical instruments. United States Patent Publication No. 2012/0022333 also describes an access port for the simultaneous use of multiple instruments. The apparatus comprises at least two ports for receiving a surgical instrument. Each port is connected to the apparatus via a ball joint to allow for a wide range of movement of the instrument. The size and number of surgical instruments that can be inserted in these access ports is, however, limited by the number of cannulas provided in the port.

United States Patent Publication No. 2010/0094227 describes a surgical access system comprising multiple parts including a removable gel cap having a gel pad through which instruments may be inserted into a body cavity either directly or through one or more trocars. The gel pad provides a flat surface, i.e., an artificial body wall, having a limited diameter to permit flexible instrument placement and range of motion.

There continues to be a need for access ports for use in minimally invasive procedures that provide flexibility to the surgeon in selecting instrument size and maximize the range of motion of the instruments extending through the access port.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a surgical access port. In accordance with an aspect of the present invention, there is provided a surgical access port comprising: a cannula comprising a first end and a second end, wherein the first end is for insertion into a target site and defines a passageway for introduction of one or more surgical instruments; at least one retainer outwardly extending circumferentially about the first end of the cannula, wherein the retainer engages an inside surface of the target site when the first end of the cannula is inserted; and a dome extending from the second end of the cannula, wherein the dome comprises an expanded diameter for receiving one or more surgical instruments.

In accordance with another aspect of the invention, there is provided a surgical access port comprising a cannula having a first end and a second end, wherein the first end is for insertion into a target site to maintain a passageway for introduction of one or more surgical instruments; at least one retainer outwardly extending circumferentially about the first end of the cannula, wherein the retainer engages an inside surface of the target site when the first end of the cannula is inserted; an elongate receptacle having a mating end for matingly engaging the second end of the cannula; a dome extending from the receptacle at an end opposite from the mating end, wherein the dome comprises an expanded diameter for receiving one or more surgical instruments.

In accordance with another aspect of the invention, there is provided a method for performing a minimally invasive surgical procedure, the method comprising: positioning the access port, of the present invention, in a target site of a patient; and inserting one or more surgical instruments through the dome of the access port and into the target site.

BRIEF DESCRIPTION OF THE FIGURES

FIGS. 6A and 6B are cross-sectional side views of an access port according to embodiments of the present invention showing a deflated and inflated state of a retainer, respectively;

DETAILED DESCRIPTION OF THE INVENTION

Definitions

Figure 1:
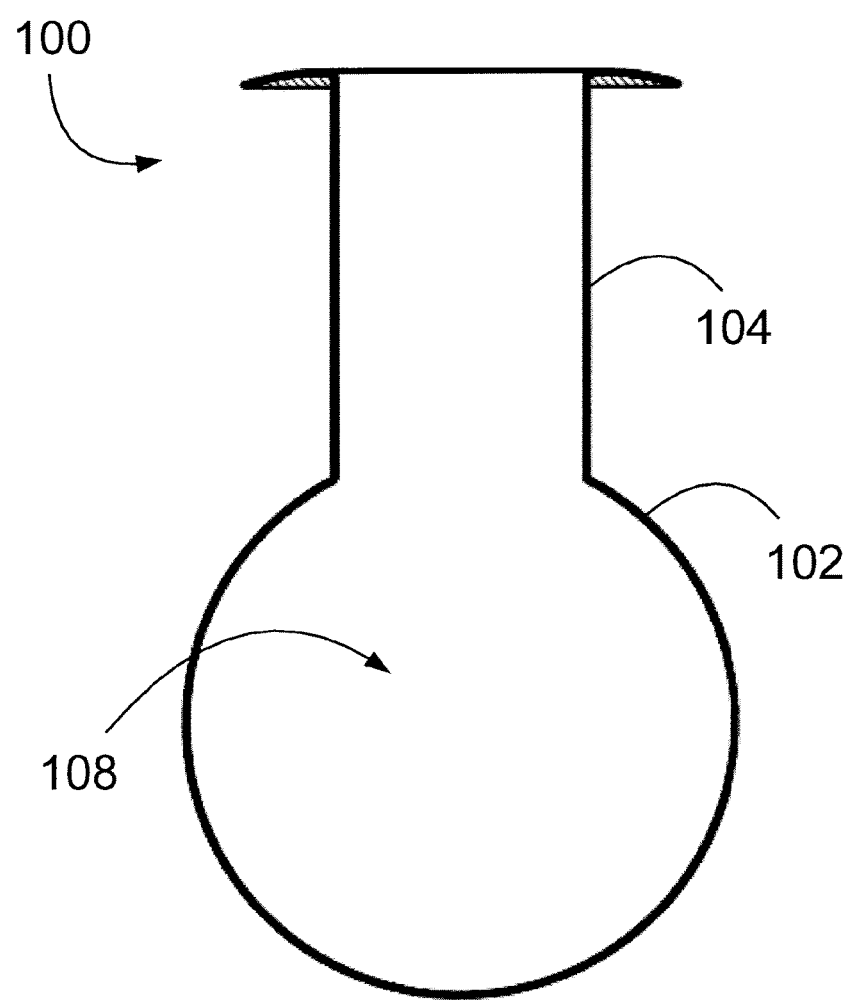
FIG. 1 is a perspective view of an access port according to embodiments of the present invention showing the access port inserted at a target site.

The terms "subject" and "patient" as used herein refer to an animal in need of treatment.

The term "animal" as used herein, includes, but is not limited to, mammals including humans.

The terms "surgical instrument(s)" and "instrument(s)", as used herein, refer to any medical instrument used in minimally invasive surgical procedures and can include, but is not limited to, standard hand instruments and articulating instruments.

The terms "minimally invasive surgery" and "minimally invasive surgical procedure(s)", as used herein, refer to surgery performed through one or more small incisions in a patient's body or through a natural orifice such as the oral cavity, nasal passages, the navel, the vagina, and the anus, and includes endoscopic and/or laparoscopic procedures.

The terms "target site" and "target cavity", as used herein, refers to the location in the patient's body where the minimally invasive surgical procedure is to occur and can include, but is not limited to, the abdominal cavity and the rectum.

The term "tissue tract", as used herein, refers to the region of tissue through which instruments must pass through to reach the target site or target cavity to conduct the minimally invasive surgical procedure.

As used herein, the term "about" refers to a +/−10% variation from the nominal value. It is to be understood that such a variation is always included in any given value provided herein, whether or not it is specifically referred to.

Unless defined otherwise, all technical and scientific terms used herein have the same meaning as commonly understood by one of ordinary skill in the art to which this invention belongs.

The access ports according to the present invention comprise an elongate cannula having a first end and a second end, a retainer coupled to the first end of the elongate cannula to fix the first end of the cannula within a tissue tract, and an enclosed dome extending from the second end of the elongate cannula for receiving surgical instruments. Access ports of the present invention comprise a minimal number of cooperating parts to provide simplicity in design, cost effectiveness in manufacture, and facility in cleaning of the access port for reuse. According to some embodiments of the present invention, the access port is a single integrated unit. In other embodiments, the access port is comprised of two separable cooperating parts.

An access port according to embodiments of the present invention are for use, for example, in single port minimally invasive surgical procedures such as in single incision and/or limited port laparoscopic surgical procedures, including for example, abdominal, trans-navel, trans-vaginal, and trans-anal procedures. Access ports according to embodiments of the present invention can simultaneously accommodate multiple instruments in a range of sizes. As well, access ports according to embodiments of the present invention, further permit translational and angular degrees of freedom for instruments, thereby, providing a range of motion of the instruments extending through the access port.

Due to this flexibility provided to the operating surgeon, the access ports of the present invention are suitable for use in trans-endoscopic procedures or trans-anal minimally invasive surgery (TAMIS), for example, to treat such pathologies as polyps and small (T1) tumours typically located within the mid to upper area of the rectum. Procedures, such as TAMIS, generally involve the insertion of multiple surgical instruments into the anal canal as well as insufflation gases that create a more accessible work area. According to embodiments of the present invention, the access port comprises a self-sealing material such that the access port is in substantial sealed engagement with an inserted surgical instrument so as to maintain the gas pressure during the surgical procedure.

Figure 2:
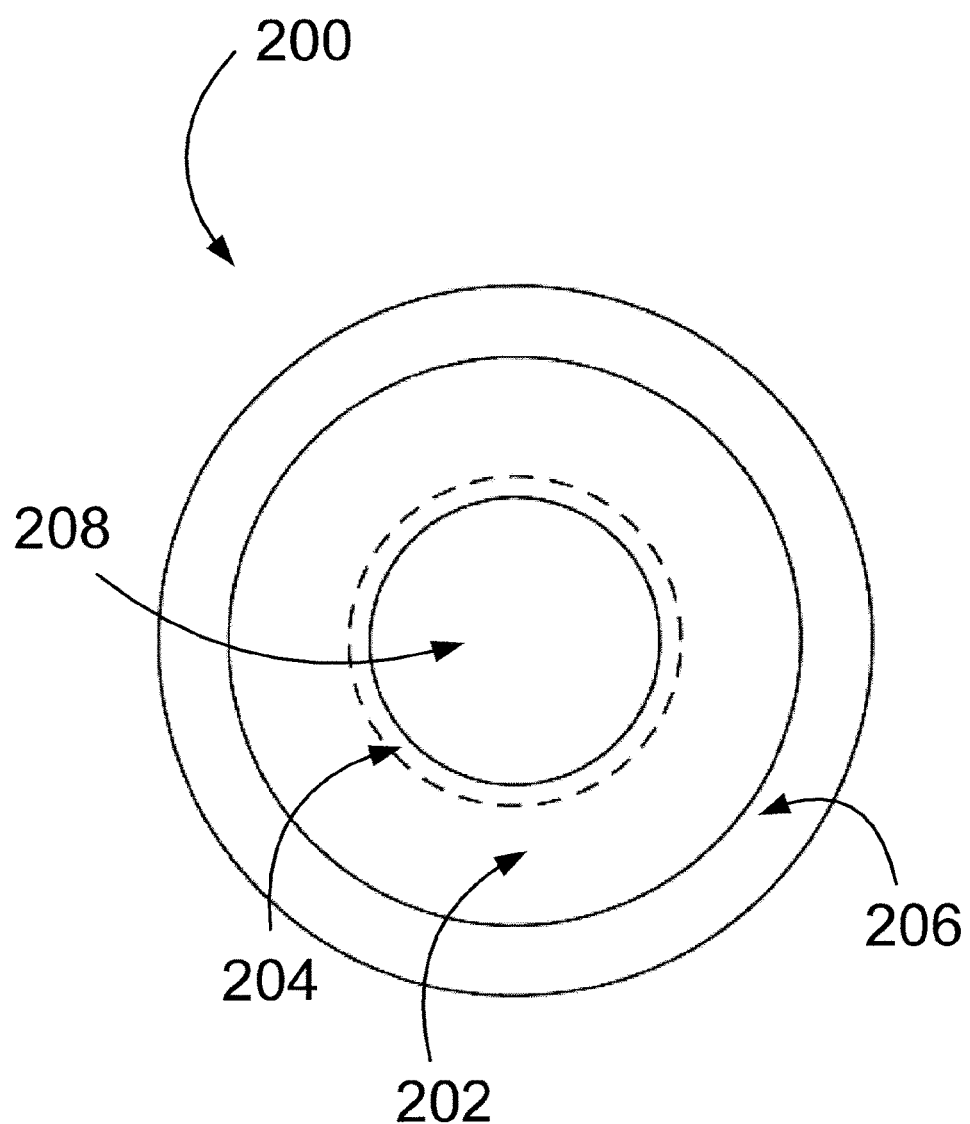
FIG. 2 is a cross-sectional end view of an access port according to embodiments of the present invention.

Referring now to the drawings, in which like reference numerals identify identical or substantially similar parts throughout the several views, FIG. 1 illustrates a cross-sectional side view of an access port 100 inserted at a target site according to embodiments of the present invention. Access port 100 includes an elongate cannula 104 having a first end and a second end, a retainer (not shown) coupled to the first end of the elongate cannula 104 to fix the first end of the cannula 104 at the target site when inserted, and an enclosed dome 102 extending from the second end of the elongate cannula 104 for receiving surgical instruments. As illustrated in FIG. 2, the cannula 204 defines a lumen 208, the diameter of which is expanded by the dome 202 at the second end of the cannula 204.

Cannula

Figure 3:
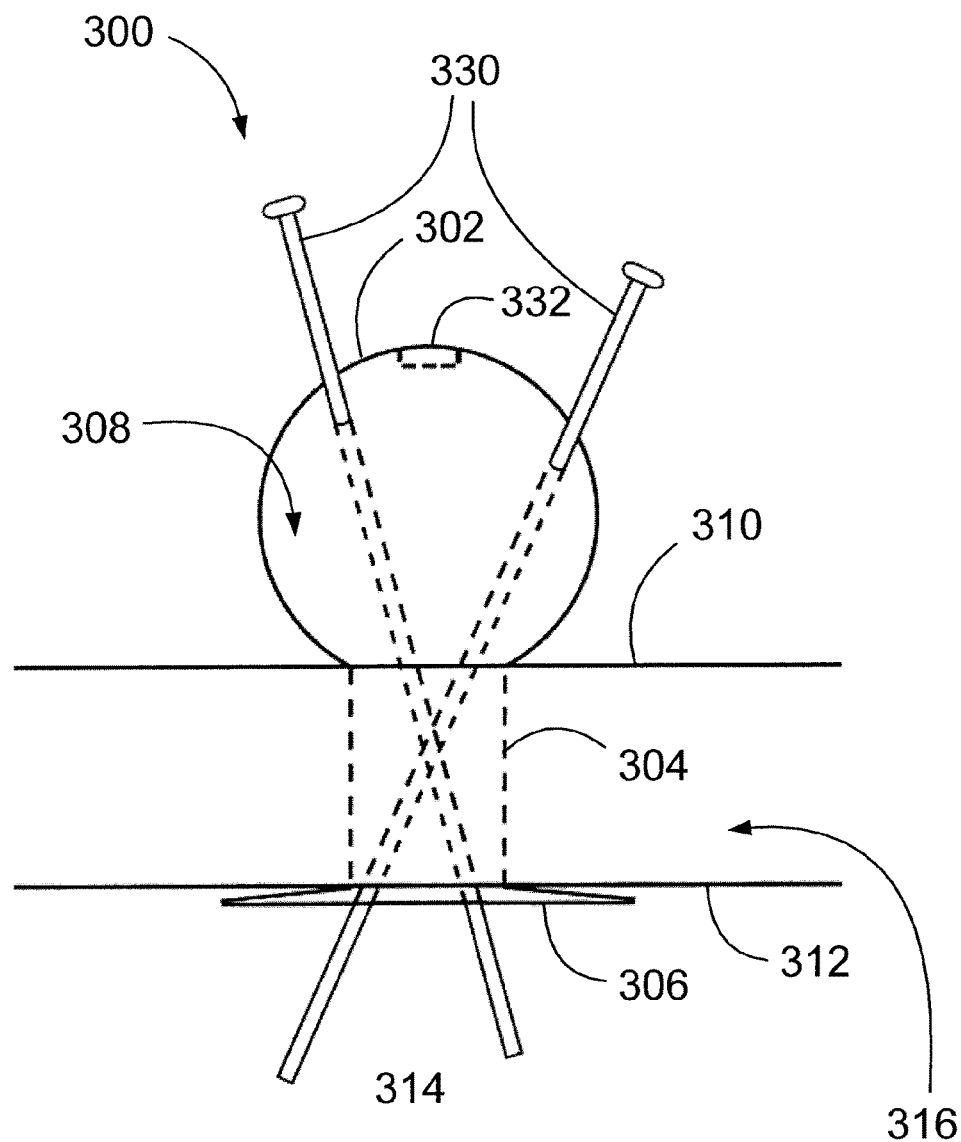
FIG. 3 is a perspective view of an access port according to embodiments of the present invention showing the access port inserted through a tissue tract at an insertion site with instruments inserted.

Referring to FIG. 3, the cannula 304 comprises an elongate, tubular body, dimensioned to accommodate one or more instruments 330 inserted therethrough. When inserted, the cannula 304 maintains a passageway through the tissue tract to facilitate the introduction and manipulation of the inserted instruments 330 in the target cavity 314. The cannula 304 protects the adjacent tissues from abrasion, tearing, and/or incised damage caused by insertion and manipulation of multiple surgical instruments 330. The cannula 304 comprises a resilient, semi-rigid, elastomeric, material, that is biologically compatible. Depending on the particular embodiment, the cannula 304 can be composed of one or more materials that permit compression to facilitate installation of the cannula 304 into an insertion site, for example, at least one of rubber, synthetic rubber, silicone, non-latex silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene), perfluoroelastomoer (Kalrez®), and the like. Some embodiments comprise a composite, for example, a multilayer structure and/or a plurality of sheets of one or more polymer materials. For example, some embodiments comprise outer surfaces and/or sheets providing desirable functionality, for example, mechanical strength, abrasion resistance, antimicrobial properties, and the like.

The dimensions of the cannula 304 will vary according to the particular use. Embodiments of the present invention can be sized for insertion into different types of target sites, for example, single incision into abdominal cavities, trans-navel, trans-vaginal, and trans-anal orifices. In addition, embodiments can be sized for insertion into juvenile subjects or into adult subjects. As well, embodiments of the present invention can be sized for use in human subjects or animal subjects in veterinary applications. In some embodiments, for example in trans-anal procedures, the cannula 304 can be relatively short because the cannula 304 need only access the rectum which for a human adult is typically 12 cm in length. Accordingly, in some embodiments the cannula 304 comprises a length of about 1.5 cm, 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, or any length therebetween. Similarly, the diameter of the cannula 304 can vary depending on the particular use. In some embodiments, the cannula 304 can have an outer diameter of about 1.5 cm, 2.0 cm, 2.5 cm, 3.0 cm, 3.5 cm, 4.0 cm, 4.5 cm, 5.0 cm, 5.5 cm, 6.0 cm, or any diameter therebetween.

Dome

The dome 302 of the access port 300 extends from the second end of the elongate cannula 304 to enclose the lumen 308. The dome 302 refers to a region of expanded diameter at one end of the cannula 304, for receiving surgical instruments 330, and may comprise a variety of shapes. For example, the dome 302 may be in the shape of a bulb, a round globe, a symmetrical ellipse, an asymmetrical ellipse, an elongate balloon with a spherical end, an elongate balloon with a tapered end, among other shapes. The shape of the dome 302 is not essential to the practice of the invention, rather, it is the expansion of the diameter, and corresponding surface area, of the access port 300 at the region of the dome 302 portion that permits the accommodation of multiple instruments 330 in the access port 300 with a wide range of movement. Accordingly, the dimensions of the dome 302 can be selected based on the number and size of instruments to be used in a procedure, and the desired range of movement required.

The dimensions of the access port 300 in accordance with the present invention, including the diameter of the dome 302 can be selected as needed for the particular use. Accordingly, embodiments of the dome 302 have an inside diameter, measured at its widest point, of at least 40% greater than the inside diameter of the second end of the cannula 304. In some embodiments of the access port 300 of the present invention, the dome 302 has an inside diameter, measured at its widest point, that is between about 1.4 times and 5.0 times greater than the inner diameter of the second end of the cannula 304. In other embodiments, the dome 302 has an inside diameter, measured at its widest point, that is about 1.4 times, 1.75 times, 2.0 times, 2.5 times, 3.0 times, 3.5 times, 4.0 times, 4.5 times, 5.0 times, or any value therebetween, greater than the inner diameter of the second end of the cannula 304. Similarly, the length of the dome 302, measured from its point of attachment with the second end of the cannula to the opposite end of the dome, can vary depending on the particular use. In some embodiments the length of the dome 302 is between about 3.0 cm and 5.0 cm. In other embodiments, the length of the dome 302 is about 3.0 cm, 3.5 cm, 4.0 cm, 4.5 cm, 5.0 cm, or any length therebetween.

The dome 302 can be molded integrally with the cannula 304 as a single integrated unit. Accordingly, the dome 302 can comprise the same material as the cannula 304. Alternatively, the dome 302 can comprise a more pliable, resilient, material for enhanced flexibility. For example, the dome 302 can comprise rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene also referred to as neoprene, perfluoroelastomer exemplified by Kalrez® (Kalrez is a registered trademark of E.I. Du Pont de Nemours and Co. Corp., Wilmington, Del., USA), and the like, or any combination thereof. Some embodiments may comprise a composite, for example, a multilayer structure and/or a plurality of sheets of one or more polymer materials. For example, some embodiments can comprise outer surfaces and/or sheets providing desirable functionality, for example, mechanical strength, abrasion resistance, antimicrobial properties, and the like.

The dome 302 can comprise a self-sealing material to provide a gas tight seal around a variety of shapes and sizes of instruments 330. When inserted through the dome 302, the dome 302 sealingly engages with the instrument 330 at the point of insertion. When the instrument is removed from the dome 302, the dome 302 self-seals to form a zero seal at the site of insertion. In this way, in procedures where insufflation gases are employed for example, embodiments of the access port 300 maintain pneumoperitoneum during multiple instrument exchanges and substantially prevent unintentional loss of pneumoperitoneum. Moreover, embodiments of the dome 302 are deformable without losing physical integrity, and while maintaining substantially gas tight seal with any instrument extending therethrough, as well as self-sealing upon removal of any instruments extending therethrough. Accordingly, embodiments of the dome 302 permit angular or pivotal ranges of movement for the instruments 330 passing through the dome 302, thereby permitting wide triangulation of instruments inserted therethrough. Due to the expanded diameter and surface area created by the dome 302, greater spacing apart of multiple instruments 330 is made available to facilitate precise manipulation of instruments 330 during surgical procedures. Accordingly, the surgeon has flexibility in determining the placement and repositioning of instruments in the dome 302 as well as flexibility in selecting the size of instruments 330 to be inserted.

In some embodiments, the dome 302 comprises a sealable trap door 332 positioned in the dome 302 to allow for removal of excised material, for example, from within the target cavity 314. Exemplary materials which a surgeon may wish to remove from a target cavity 314 during a surgical procedure may include, for example, tissue, tumours, bone fragments, calcified minerals, conduits, foreign materials and the like. In some embodiments the trap door 332 is positioned on the dome 302 substantially opposite the second end of the cannula 304 to easily access the target cavity 314. The trap door 332 can be integrally moulded into the dome 302 or may be affixed. In some embodiments, the trap door 332 is sealable such that a gas-tight seal is restored after opening and closing of the trap door 332, thereby allowing the body cavity to be re-insufflated with gases.

Retainer

Whether inserted in an incision point or a natural orifice, the tissue tract 316 at a target insertion site continually exerts an inward force on the access port 300 of the present invention. This constant inward force can provide sealing of the access port 300 at the insertion site thereby inhibiting escape of insufflation gas from the target cavity. The continual inward force exerted on the access port 300 at the insertion site, however, can also result in difficulty in positioning the access port 300 and/or accidental dislodgement of the access port 300 during a procedure.

Access ports 300 of the present invention comprise a retainer 306 for anchoring the access port 300 in position when inserted at a target insertion site. The retainer 306 is generally an outwardly facing structure extending around the circumference at the first end or approximate the first end of the cannula 304. When the cannula 304 is inserted through the tissue tract 316, the dome 302 engages with the outside surface 310 of the target cavity 314 in cooperation with the retainer 306, engaged with the inside surface 312 of the target cavity 314, to anchor the access port 300 in position at the insertion site.

Figure 4A:
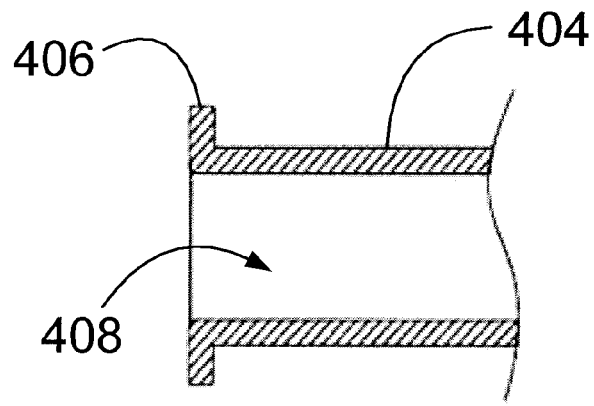
FIGS. 4A-4C are partial cross-sectional side views of an access port according to embodiments of the present invention.
Figure 4B:
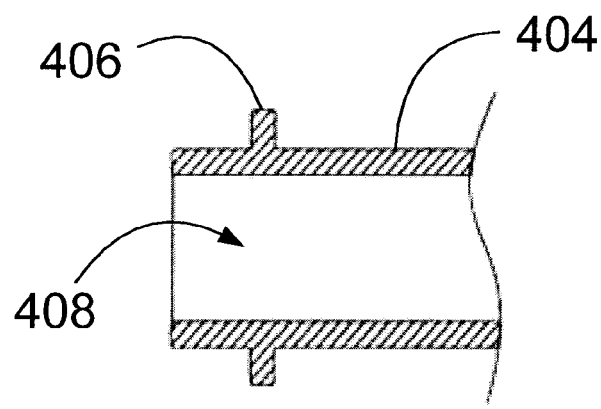
Figure 4C:
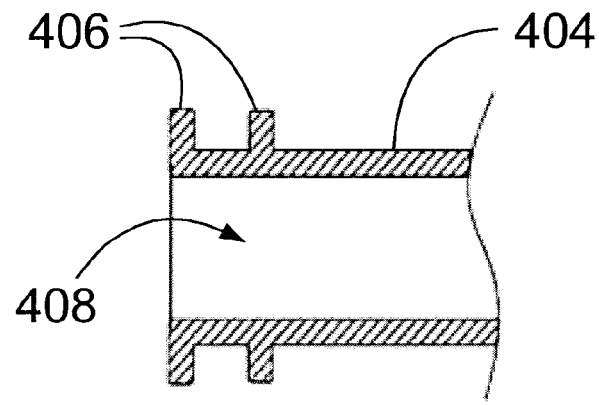

According to one embodiment of the present invention, as illustrated in FIG. 4, the retainer 406 may be a rim outwardly extending continuously or discontinuously around the circumference of the first end of the cannula 404. The retainer 406 may be located flush with the first end of the cannula 404, for example as illustrated in FIG. 4A), or alternatively located along the length of the cannula 404, for example as illustrated in FIG. 4B. In some embodiments, access ports 400 of the present invention may comprise a single retainer 406 outwardly extending around the circumference of the cannula 404. In other embodiments, as illustrated in FIG. 4C access ports 400 may comprise multiple retainers 406 located along the length of the cannula 404.

According to some embodiments of the present invention, the retainer can transition between an extended state and a retracted state when in use. For example, when inserted into an insertion site, the retainer is in an extended state. In the extended state, the retainer extends around the circumference of the first end of the cannula so as to engage with the inside surface of the target cavity. During insertion or removal of the first end of the cannula through an insertion site, the retainer is in a retracted state thereby reducing its cross-sectional profile so as to facilitate insertion or removal of the access port as the first end of the cannula passes through the tissue tract.

Figure 5A:
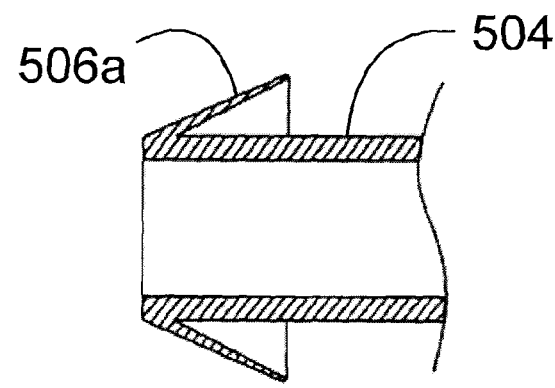
FIGS. 5A-5C are partial cross-sectional side views of an access port according to embodiments of the present invention in which exemplary states of a retainer are shown.
Figure 5B:
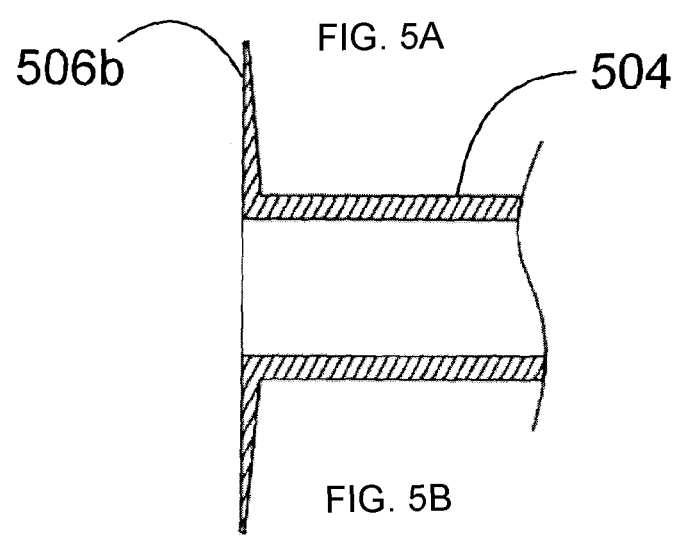
Figure 5C:
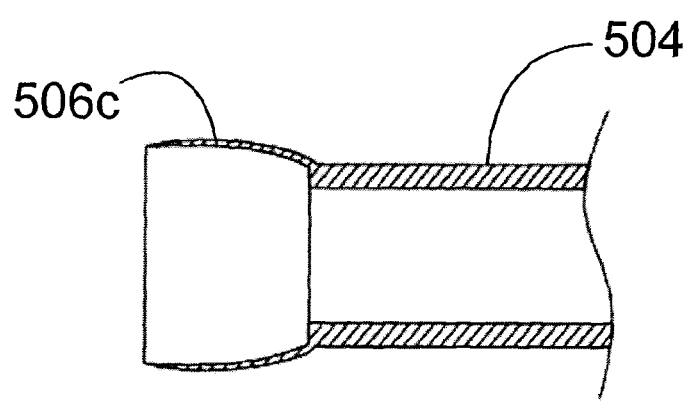

In one embodiment of the present invention, as illustrated in FIG. 5, the retainer 506a-c is a resilient flap extending continuously, or discontinuously, around the circumference at the first end or approximate the first end of the cannula 504. During insertion into an insertion site, the first end of the cannula 504 is pushed into an incision or a natural orifice. The tissue tract through which the cannula 504 is pushed, radially compresses the retainer 506a thereby causing the retainer 506a to fold back towards the cannula 504 into the retainer's 506a retracted state. Once the first end of the cannula 504 is inserted through the tissue tract, the retainer 506b reverts to an extended state to engage with the inside surface of the target cavity. A first pull force may be applied to the inserted access port to engage the extended retainer 506b with the inside surface of the target cavity. To remove the access port from a target cavity, a second pull force may be applied to the access port causing the extended retainer 506b to deform and fold outward and away from the first end of the cannula 504. The retainer 506c is thereby transitioned to a retracted state to allow disengagement from the inside surface of the target cavity and enable removal of the access port.

In another embodiment of the present invention, as illustrated in FIG. 6, the retainer 606 is an inflatable/deflatable balloon cuff provided about the outer circumference at the first end or approximate the first end of the cannula 604. The retainer 606 is in fluid communication with a sealable port 642 which enables the balloon cuff to be inflated. The sealable port 642 may further comprise an integral valve 644 to release fluid from the balloon cuff enabling its deflation. When in use, the retainer 606a can be deflated to a retracted state to facilitate insertion of the first end of the cannula 604 into an insertion site. Once in position, the balloon cuff may be inflated by an air supply delivered through the sealable port 642, to transition the retainer 606b to an extended state. The inflated balloon cuff of the retainer 606b engages with the inside surface of the target cavity to anchor the access port 600 in position. To remove the access port 600 from the insertion site, the balloon cuff of the retainer 606a may be deflated by releasing air through the sealable port 642 to revert the retainer 606a to its retracted state and allowing removal of the access port 600 from the insertion site.

Figure 7:
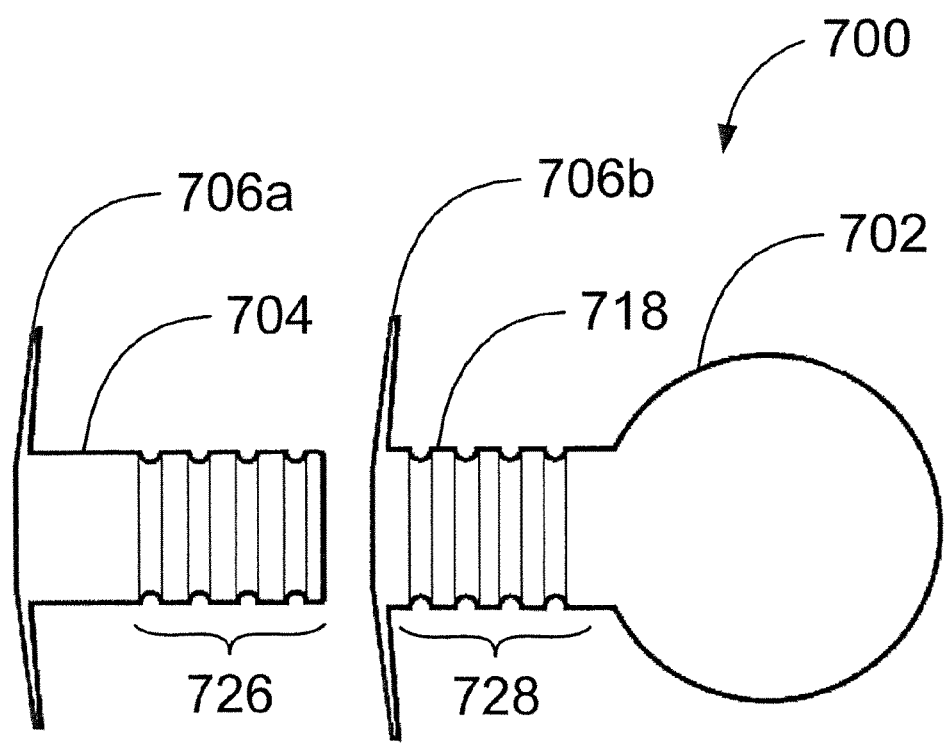
FIG. 7 is a cross-sectional side view of a two-piece access port according to embodiments of the present invention.
Figure 8:
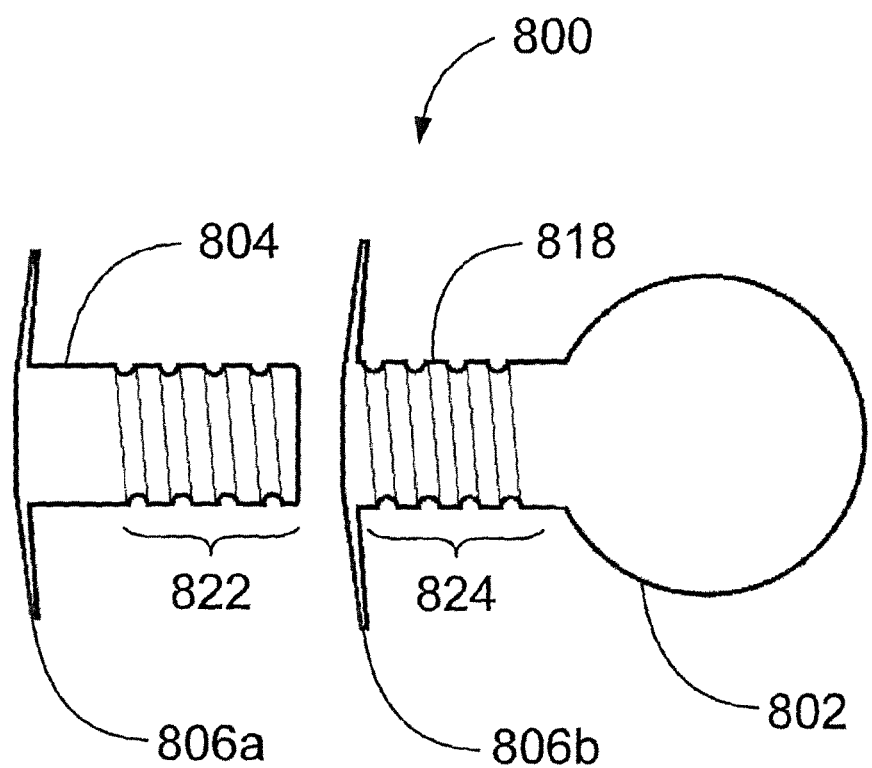
FIG. 8 is a cross-sectional side view of a two-piece access port according to embodiments of the present invention.
Figure 9:
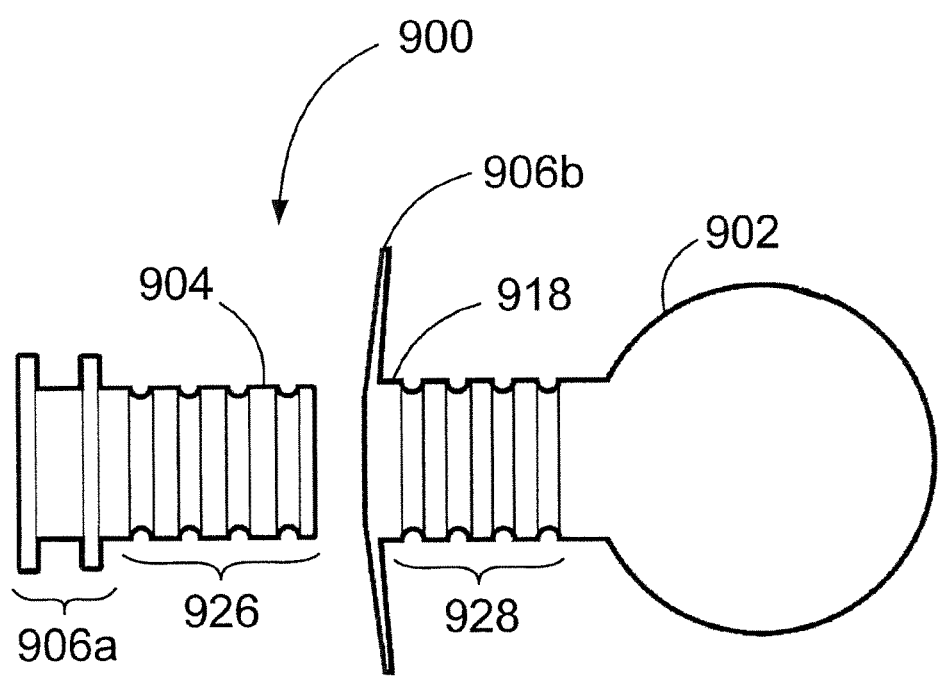
FIG. 9 is a cross-sectional side view of a two-piece access port according to embodiments of the present invention.

In other embodiments of the present invention, as illustrated in FIGS. 7, 8, and 9, the access port comprises two pieces which matingly engage to anchor the access port in position at the insertion site. Referring to FIGS. 7, 8, and 9, the first piece of the access port 700, 800, 900 comprises the cannula 704,804,904 and an inner retainer 706a, 806a, 906a at the first end of the cannula 704, 804, 904. The second piece comprises the dome 702, 802, 902 and a receptacle 718, 818, 918 extending from the dome 702, 802, 902 for engagement with the cannula 704,804,904 of the first piece. The second piece of the access port 700, 800, 900 may optionally further comprises an outer retainer 706b, 806b, 906b located flush with the mating end of the receptacle 718,818,918 and opposite from the dome 702, 802, 902. As discussed above, when the cannula 704, 804, 904 of the first piece is inserted through the tissue tract the inner retainer 706a, 806a, 906a engages with the inside surface of the target cavity. Once the first piece has been inserted into the target cavity, the cannula 704, 804, 904 of the first piece and the receptacle 718, 818, 918 of the second piece matingly engage at the outside surface of the target cavity at the insertion site. When the two pieces of the access port 700, 800, 900 are matingly engaged, the inner 706a, 806a, 906a and outer 706b, 806b, 906b retainer cooperate on either side of the tissue tract to provide a tight seal and anchor the access port 700, 800, 900 in position at the insertion site.

The cannula 704, 804, 904 of the first piece and the receptacle 718, 818, 918 of the second piece each comprise mating apertures for releasable engagement. For example, the cannula 704, 904 may comprise a series of outward-facing ridges and grooves 726, 926 that matingly engage with corresponding inward-facing ridges and grooves 728, 928 displayed on the receptacle 718, 918 extending from the second piece. Alternatively, as illustrated in FIG. 8, the cannula 804 may comprise outward facing male threads 822 that matingly engage with corresponding female threads 824 displayed on the receptacle 818 extending from the second piece, which screw together for releasable engagement. In some embodiments, the threads 822 and 824 may be aluminum bonded on the respective cannula 804 and receptacle 818. Those skilled in these arts will be aware of and will understand that other quick connect/disconnect options for releasably engaging the cannula 704 and 804 and the receptacle 718 and 818 can be provided.

As discussed above, the inner and/or outer retainer of access ports of the present invention can take a variety of forms. For example, as illustrated in FIGS. 7 and 8, the inner and/or outer retainer 706a, 806a, 706b and 806b, may be a resilient flap extending continuously, or discontinuously, around the circumference of the respective piece. Alternatively, for example, the inner and/or outer retainer may be one or more rims outwardly extending continuously or discontinuously around the circumference of the respective piece. As illustrated in FIG. 9, the access port 900 may comprise a combination of different types of retainer 906a and 906b. For example, as shown, the inner retainer 906a may comprise one or more rims outwardly extending circumferentially about the first end of the cannula 904 and the outer retainer 906b may comprise a resilient flap.

In order to secure the access port at the insertion site, the outer diameter of the retainer, including an inner retainer or an outer retainer, is larger than the outer diameter of the respective cannula or receptacle. In some embodiments of the access port of the present invention, the outer diameter of the retainer is between about 0.5% to about 50% larger than the outer diameter of the respective cannula or receptacle. In other embodiments of the invention, the width of the retainer measured from the point of attachment to the respective cannula or receptacle to the outside edge of the retainer, is between about 0.5 cm to 2.5 cm. In further embodiments, the width of the retainer is 0.5 cm, 1.0 cm 1.5 cm, 2.0 cm, or any width therebetween.

Access ports in accordance with the invention can serve many purposes, only one of which is use in minimally-invasive surgical procedures. It should be appreciated by those skilled in the art, that access ports in accordance with the invention can be used wherever access, particularly sealable access, into a body cavity is needed.

The specific dimensions of access ports in accordance with the invention can be selected as needed. Specifically, it is envisioned that a wide variety of sizes will be available to a user to enable the user to select the most appropriately dimensioned device for the patient and procedure at hand. The overall dimensions of access ports in accordance with the invention can vary, as well as the relative dimensions of the dome, cannula, and retainer portions of the access port, and the like.

To gain a better understanding of the invention described herein, the following example is set forth. It will be understood that the example is intended to describe illustrative embodiments of the invention and is not intended to limit the scope of the invention in any way.

EXAMPLES

Example 1

Figure 10A:
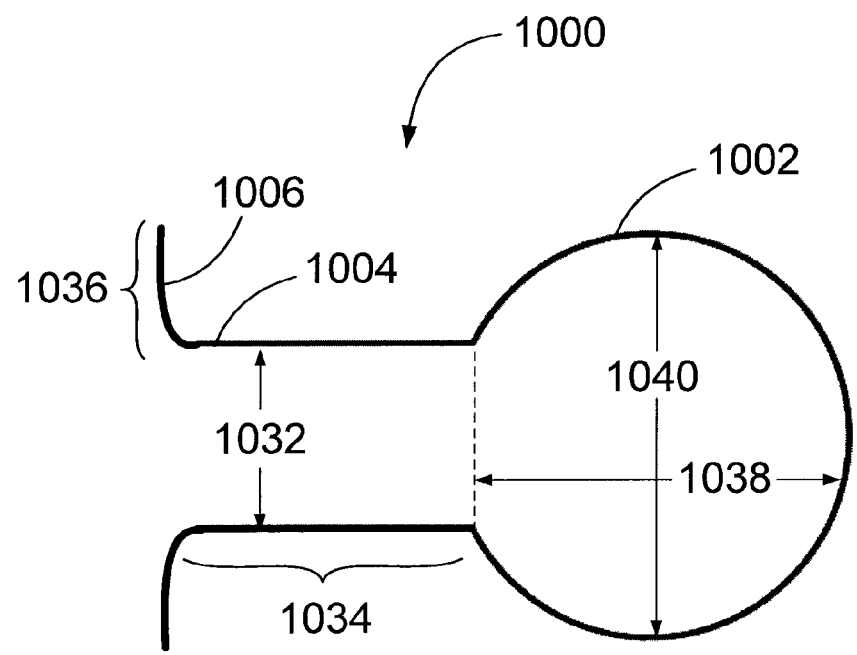
FIG. 10A is a cross-sectional side view of an example access port according to embodiments of the present invention.
Figure 10B:
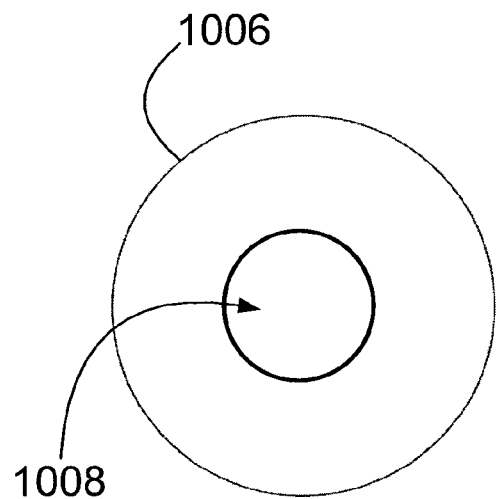
FIG. 10B is an end view of an example access port according to embodiments of the present invention.

FIG. 10A illustrates a cross-sectional side view of an example access port 1000 according to an embodiment of the present invention. FIG. 10B illustrates an end view of the access port 1000 as shown in FIG. 10A. The access port 1000 is a single integrated unit comprising an elongate cannula 1004 having a first end and a second end, a retainer 1006 coupled to the first end of the elongate cannula 1004 to fix the first end of the cannula 1004 within a tissue tract, and an enclosed dome 1002 extending from the second end of the elongate cannula 1004 for receiving surgical instruments. The access port 1000 can be made of rubber, silicon, or any other resilient, semi-rigid, elastomeric, material, that is biologically compatible. The dimensions of the access port 1000 can be sized for its particular desired use. For use in endoscopic microsurgery procedures in adult humans, for example, the access port 1000 has a cannula 1004 that is between about 1.5 cm to 8.5 cm in length 1034, and has a diameter 1032 between about 1.5 cm to 4.5 cm. The access port 1000 has a retainer 1006 comprising a resilient flap that extends continuously around the circumference at the first end of the cannula 1004. The retainer 1006 has a width 1036, measured from the point of attachment to the first end of the cannula 1004, of between about 0.5 cm to 2.5 cm. The dome 1002 is shaped as illustrated to enclose the lumen 1030 of the access port 1000. The dome 1002 has a diameter 1040 of between about 5.0 cm to about 8.0 cm, and a length 1038 of between about 3.0 cm to about 5.0 cm.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. A surgical access port comprising:
   a cannula comprising a first end and a second end, wherein the first end is insertable into a target site, the cannula defining a passageway for introduction of one or more surgical instruments;
   at least one retainer outwardly extending circumferentially about the first end of the cannula, the at least one retainer having an inner retainer diameter, wherein the retainer is adapted to engage an inside surface of the target site when the first end of the cannula is inserted into the target site;
   an elongate receptacle having a mating end for matingly engaging the second end of the cannula; and
   a self-sealable, deformable, and passageway-enclosing dome extending from the receptacle at an end opposite from the mating end, the dome comprising a self-sealable material through which one or more surgical instruments are directly insertable at multiple insertion locations, the dome having an inner diameter at its widest point greater than the inner retainer diameter and a manipulation area permitting angular or pivotal ranges of movement for the one or more surgical instruments within the manipulation area, and the dome sealingly engageable with the one or more surgical instruments introduced therethrough and self-sealable to form a zero seal at the multiple insertion locations when the one or more surgical instruments are removed.

2. The surgical access port according to claim 1 wherein the receptacle further comprises a second retainer outwardly extending circumferentially about the mating end of the receptacle.

3. The surgical access port according to claim 1, wherein the cannula and the receptacle comprise cooperating mating features for releasable engagement.

4. The surgical access port according to claim 3, wherein the mating features are a series of matingly engaging ridges and grooves.

5. The surgical access port according to claim 3, wherein the mating features are a series of matingly engaging screw threads.

6. The surgical access port according to claim 5, wherein the screw threads are aluminum bonded on the respective cannula and receptacle.

7. The surgical access port according to claim 1, wherein the dome is a bulb, a round globe, a symmetrical ellipse, an asymmetrical ellipse, an elongate balloon with a spherical end, or an elongate balloon with a tapered end.

8. The surgical access port according to claim 1, wherein the dome's inner diameter, measured at its widest point, is at least 40% greater than a diameter of the cannula.

9. Use of the access port according to claim 1 for performing a minimally invasive surgical procedure.

10. A surgical access port comprising:
a cannula comprising a first end and a second end, wherein the first end is insertable into a target site, the cannula defining a passageway for introduction of one or more surgical instruments;
at least one retainer outwardly extending circumferentially about the first end of the cannula, the at least one retainer having an inner retainer diameter, wherein the retainer is adapted to engage an inside surface of the target site when the first end of the cannula is inserted into the target site; and
an elongate receptacle having a mating end for matingly engaging the second end of the cannula; and
a self-sealable, pliable, and passage-way enclosing dome extending from the receptacle at an end opposite from the mating end, the dome comprising a self-sealable material through which one or more surgical instruments are directly insertable at multiple insertion locations, the dome having an inner diameter at its widest point greater than the inner retainer diameter and a manipulation area permitting angular or pivotal ranges of movement for the one or more surgical instruments within the manipulation area, and the dome sealingly engageable with the one or more surgical instruments introduced therethrough and self-sealable to form a zero seal at the multiple insertion locations when the one or more surgical instruments are removed.

11. The surgical access port according to claim 10, wherein the receptacle further comprises a second retainer outwardly extending circumferentially about the mating end of the receptacle.

12. The surgical access port according to claim 10, wherein the cannula and the receptacle comprise cooperating mating features for releasable engagement.

13. The surgical access port according to claim 12, wherein the mating features are a series of matingly engaging ridges and grooves.

14. The surgical access port according to claim 12, wherein the mating features are a series of matingly engaging screw threads.

15. The surgical access port according to claim 14, wherein the screw threads are aluminum bonded on the respective cannula and receptacle.

16. The surgical access port according to claim 10, wherein the dome is a bulb, a round globe, a symmetrical ellipse, an asymmetrical ellipse, an elongate balloon with a spherical end, or an elongate balloon with a tapered end.

17. The surgical access port according to claim 10, wherein the dome's inner diameter, measured at its widest point, is at least 40% greater than a diameter of the cannula.

18. Use of the access port according to claim 10 for performing a minimally invasive surgical procedure.

19. The surgical access port according to claim 10, wherein the access port comprises an elastomeric material.

* * * * *